United States Patent [19]

Tsoglin et al.

[11] Patent Number: 5,735,284
[45] Date of Patent: Apr. 7, 1998

[54] METHOD AND SYSTEM FOR NON-INVASIVE DETERMINATION OF THE MAIN CARDIORESPIRATORY PARAMETERS OF THE HUMAN BODY

[75] Inventors: Alexander Tsoglin, Tel-Aviv; Efim Frinerman, Bat-Yam, both of Israel

[73] Assignee: N.I. Medical Ltd., Tel-Aviv, Israel

[21] Appl. No.: 490,047

[22] Filed: Jun. 13, 1995

Related U.S. Application Data

[63] Continuation-in-part of Ser. No. 82,606, Jun. 24, 1993, Pat. No. 5,469,859.

[30] Foreign Application Priority Data

Jun. 24, 1992 [IL] Israel ............... 102300

[51] Int. Cl.⁶ ............................................. A61B 5/04
[52] U.S. Cl. ............................................. 128/696; 128/723
[58] Field of Search ............................ 128/693, 695, 128/696, 723, 734; 364/413.02, 413.07

[56] References Cited

U.S. PATENT DOCUMENTS

| Re. 30,101 | 9/1979 | Kubicek et al. . |
|---|---|---|
| 4,059,169 | 11/1977 | Hagen . |
| 4,116,231 | 9/1978 | Matsuo . |
| 4,182,314 | 1/1980 | Boughton . |
| 4,379,460 | 4/1983 | Judell . |
| 4,450,527 | 5/1984 | Sramek . |
| 4,781,201 | 11/1988 | Wright et al. . |
| 4,807,638 | 2/1989 | Sramek . |
| 4,823,797 | 4/1989 | Heinze et al. . |
| 4,905,705 | 3/1990 | Kizakevich et al. . |
| 4,911,175 | 3/1990 | Shizgal . |
| 4,919,145 | 4/1990 | Marriott . |
| 5,063,937 | 11/1991 | Ezenwa et al. . |
| 5,241,963 | 9/1993 | Shankar ...................... 128/693 |
| 5,309,917 | 5/1994 | Wang et al. . |

FOREIGN PATENT DOCUMENTS

| 50-4378 | 4/1975 | Japan . |
|---|---|---|
| 53-148892 | 12/1978 | Japan . |
| 54-1218 | 1/1979 | Japan . |
| 60-259242 | 12/1985 | Japan . |
| 62-2792 | 2/1987 | Japan . |
| 1644902 | 4/1991 | U.S.S.R. . |
| 82/01122 | 4/1982 | WIPO . |
| 90/00367 | 1/1990 | WIPO . |

OTHER PUBLICATIONS

Spinale et al., "Relationship of bioimpedance to thermodiluation and echocardiographic measurements of cardiac function", Critical Care Medicine, vol. 18, No. 4, pp. 414-418, Apr. 1990.

(List continued on next page.)

*Primary Examiner*—William E. Kamm
*Attorney, Agent, or Firm*—Helfgott & Karas, P.C.

[57] ABSTRACT

A method and a system for non-invasively determining at least one main cardiorespiratory parameter of an individual, such as the Stroke Volume, at least one parameter characterizing balance of the extracellular fluid in the body (such as the Index Balance), and for diagnostics of blood circulatory problems and/or failures of cardiac functions. The method for determining the main cardiorespiratory parameter comprises the steps of attaching at least two electrodes to the individual's body in a manner enabling to obtain electrical bioimpedance measurements of the whole individual's body, passing an alternating current with a stable and constant amplitude through the electrodes, measuring the integral bioimpedance as the result of the current flow; simultaneously separating an active component from the integral bioimpedance; calculating the cardiorespiratory parameter of the individual from the obtained active component, using an empiric formula applicable to integral bioimpedance measurements. The calculation is based on obtaining a number of values of the parameter for a number of cardia cycles during a respiratory cycle, and computing an average of the cardiorespiratory parameter during a single respiratory cycle.

16 Claims, 7 Drawing Sheets

OTHER PUBLICATIONS

Jewkes, et al., "Non-invasive Measurement of Cardiac Output by Thoracic Electrical Bioimpedance: A Study of Reproducibility and Comparison With Thermodilution, British Journal of Anaesthesia, vol. 67, pp. 788–794, 1991.

Sramek, "Cardiac Output by Electrical Impedance", Med. Elect., pp. 93–97, Apr. 1982.

Kubicek, et al., "The Minnesota impedance cardiograph-theory and applications", Biomedical Engineering, vol. 9, No. 9, pp. 410–416, Sep. 1974.

Kushner et al., "Estimation of total body water by bioelectrical impedance analysis, Amer. Journal of Clin. Nutr., vol. 44, pp. 417–424, Sep. 1986.

Lukaski, et al., "Assessment of fat-free mass using bioelectrical impedance measurements of the human body", Amer. Journal of Clin. Nutr., vol. 41, pp. 810–817, Apr. 1985.

Bernstein, "A new stroke volume equation for thoracic electrical bioimpedance: Theory and rationale", Critical Care Medicine, vol. 14, No. 10, pp. 904–908, Oct. 1986.

Tischenko, "Sechenov Physiological Journal of the USSR", Academy of Science, USSR, vol. 49, pp. 1216–1224, 1973.

B. Tedner, "Equipment using an impedance technique for automatic recording of fluid-volume changes during haemodialysis", Med. and Bio. Eng. and Comp., vol. 21, May 1983, pp. 285–290.

H.G. Goovaerts et al., "Microprocessor-based system for measurement of electrical impedances during haemodialysis and in postoperative care", Med. and Bio. Eng. and Computing, vol. 26, No. 1, Jan. 1988, pp. 75–80.

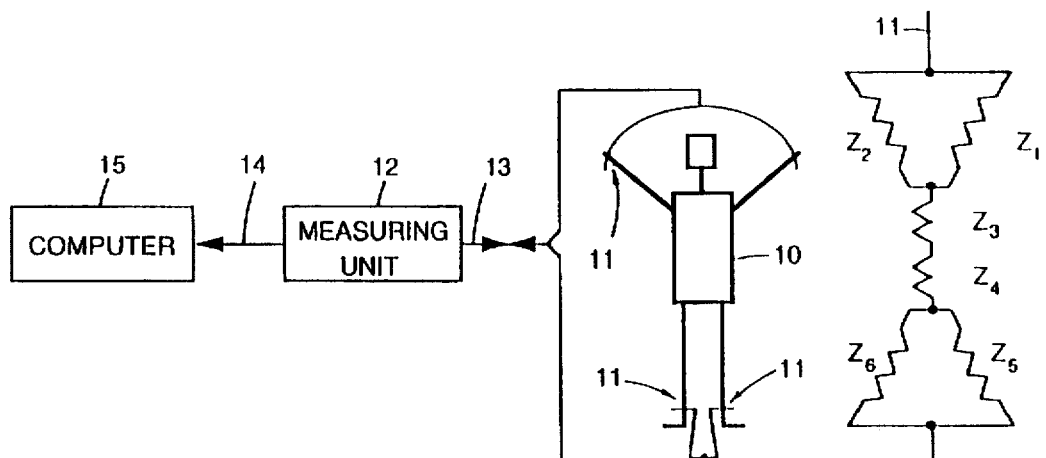
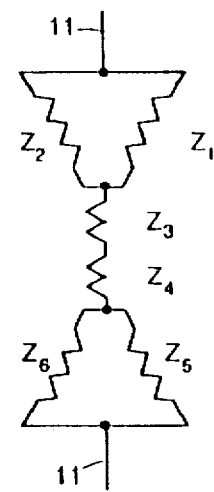
Fig. 1A  Fig. 1B
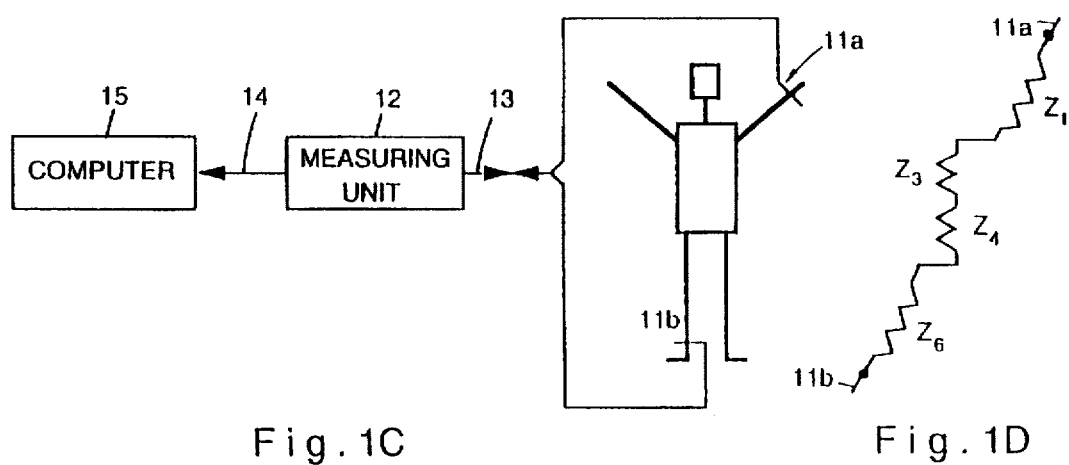
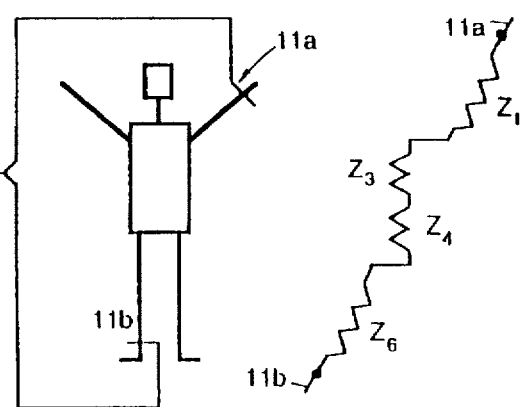
Fig. 1C  Fig. 1D
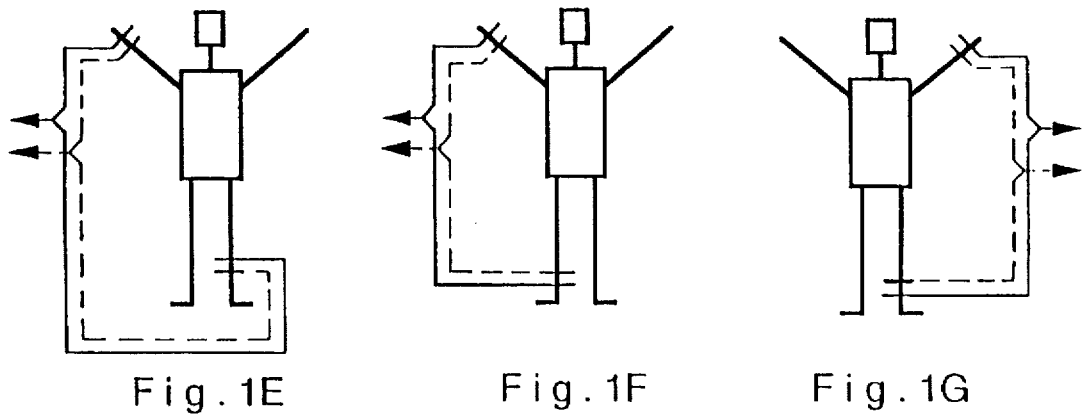
Fig. 1E  Fig. 1F  Fig. 1G

METHOD AND SYSTEM FOR NON-INVASIVE DETERMINATION OF THE MAIN CARDIORESPIRATORY PARAMETERS OF THE HUMAN BODY

FIELD OF THE INVENTION

The present invention relates to non-invasive cardiac and respiratory monitors, more particularly, to such systems for determining cardiac and respiratory performance using electrical bioimpedance measurements. It is a continuation-in-part to U.S. patent application Ser. No. 08/082,606 filed Jun. 24, 1993 and issued as U.S. Pat. No. 5,469,859 on Nov. 28, 1995.

BACKGROUND OF THE INVENTION

Thermodilution is a well-known invasive procedure for enabling a physician to determine the main hemodynamic parameters of the human body. The patients investigated are admitted to the Intensive Care Unit and have pulmonary artery catheters inserted. Ice cold saline solution is then used for the thermodilution measurements. This method is quite accurate, but it suffers from obvious disadvantages of an invasive procedure.

Several non-invasive methods intended to substitute the invasive thermodilution procedure have been disclosed in the prior art. Two such modern non-invasive methods are widely known: one being based on echocardiographic measurements, and the other being the electrical bioimpedance measurement (EBM) method.

An obvious requirement of non-invasive techniques is the correlation of their results with the readings obtained by the basic invasive method, such as thermodilution. It has been found that the echocardiographic measurements are technically unsatisfactory in many cases.

Two main types of the Electrical Bioimpedance Measurements (EBM) are known for measuring cardiac outputs:

Local (segmentary) EBM of the variations in the blood volume, provided on specific parts of the body; the technique for thoracic EBM was suggested by Kubicek W. G., et al. (Biomedical Engineering, 1979,9; 410-416) and then modified by Sramek B. B., (*Med. Elect.*, 1982, April, 93-97) and Bernstein, D. P. (*Crit. Care Med.*, 1986; 14:904-9); and Integral EBM (EBM of the whole body), enveloping practically the entire blood conducting system; the technique is described by Tischenko, M. I., (*Sechenov Physiol. J. of the USSR*, 1973; 49:1216-24). The whole body EBM technique is a priori more informative than the segmentary EBM; however, no realization thereof appropriate for reliable clinical use has been documented.

U.S. Pat. No. Re: 30,101 (William Kubicek et al.) describes an Impedance Plethysmograph. Cardiac output is measured by connecting excitation electrodes at the upper and lower ends of the thorax of a patient, and connecting measuring electrodes to the thorax between the excitation electrodes. A constant fluctuating excitation current is applied to the excitation electrodes, and any changes in impedance within the thorax are measured, whilst simultaneously measuring the beginning and the end of a systole. Cardiac output is determined by measuring the maximum decreasing impedance slope during the systole.

U.S. Pat. No. 4,450,527 (Bohumir Sramek), assigned to one of the leading companies in the field, BoMED® Medical Manufacturing Ltd., describes a non-invasive cardiac output monitor. The system disclosed there, where measurement of cardiac output is made by means of thoracic EBM, eliminates the effect of respiration from the thoracic impedance as a function of time, so as to provide continuously a signal of pulsatile thoracic impedance changes. The pulsatile thoracic impedance signal is processed to produce signals indicative of the ventricular ejection time and the maximum rate of change of the pulsatile thoracic impedance, is fed to a microprocessor in order to calculate the volume of blood pumped per stroke according to an improved systolic upstroke equation.

U.S. Pat. No. 4,807,638 (B. Sramek, assigned to BoMED®) discloses an improvement of the thoracic EBM of the U.S. Pat. No. 4,450,527. This monitor measures the electrical impedance across two segments of body tissue (thorax and legs) to provide a signal for each segment that indicates the increase in blood flow in the segment at the beginning of each cardiac cycle. The cardiac output of the patient is also measured and the cardiac index of the patient is calculated from the cardiac output.

An analysis of systems which implement Kubicek's and Sramek's method, reveals that they are not accurate for the following reasons:

1. Calculation of all the main "volume" hemodynamic parameters (Stroke volume, Cardiac output, etc.) is accomplished by using the derivative of the Impedance ($dZ/dt$), but not the measured change of the active bioimpedance component ($\delta r$), being the direct characteristics of the fluid volume.
2. Dispersion of the measuring current out of the measured segment into other parts of the body: causes errors in the measurement of stroke volume.
3. Geometry of the measured segment affects the results.
4. Errors occurring owing to the initial non-accurate electrodes' placement on the thorax, and their displacement caused by respiration.
5. Substantial calculation errors as a result of the fact, that $dZ/dt$ is determined relative to the partial thoracic impedance, but not relatively to the whole body impedance.

Moreover, these systems do not obtain and calculate parameters, characterizing the respiratory system.

Integral EBM of the whole body is a priori more informative than the segmentary EBM; however, no realization thereof appropriate for broad clinical use has been achieved till date.

The Integral EBM of the whole body was originally suggested by M. I. Tishcenko supra. This method includes applying electrodes in a manner so that the measuring current passes not through a segment, but rather through the whole body; injecting a low amplitude alternating current having a frequency of 30 KHz; measuring the whole body's impedance with an impedance plethysmograph having a measuring bridge; separation of the active component of the impedance by manual tuning, and using it for the subsequent calculations.

The above integral EBM method enables the operator to obtain information, concerning the whole cardiovascular system of the body; the main hemodynamic parameters are obtained using different empiric equations derived by M. Tishenko for the integral measurements. Owing to the larger length of the body, embraced by the electrodes, calculation errors cart be minimized. The method uses a bipolar electrode system, which is simpler and less prone to error than the tetrapolar Kubicek's system used in the segmentary type EBM method.

However, the system used by M. Tishcenko, needs to be calibrated before every measurement; it also requires tuning in order to exclude the reactive component of the impedance. The other problem is the error, caused by the reactive component, appearing between the electrodes and the skin at the place of their contact. This error is almost impossible to remove by tuning. The accuracy of the calculations completely depends on the manual adjustment, thus rendering the Tishcenko system unreliable.

The formulae of Tishcenko for calculating cardiovascular parameters are corrected only by sex parameters. However, it has been documented that the whole body impedance and, in particular, its resistive component are influenced by many other parameters, such as Hematocrit, body composition, etc.

SUMMARY OF THE INVENTION

It is an object of the present invention to provide a novel non-invasive whole body EBM method and system for the determination of the main cardiorespiratory parameters of the human body.

The invention provides by a first of its aspects, a non-invasive method for determining the main cardiorespiratory parameters of an individual. In accordance with this aspect, electrodes are applied to at least two of the individual's arms and legs, a high stability amplitude alternating current is injected through the electrode into the body, and an integral impedance curve of the body is thus obtained. An active (i.e. resistive) component is then separated from the measured whole body impedance and by employing an empiric formula applicable to integral bioimpedance measurements, the cardiorespiratory parameters of the individual being calculated from said active component, wherein the calculation is based on an average data obtained during respiration cycles.

More specifically, in accordance with the first aspect of the invention, there is provided a method for non-invasively determining at least one main cardiorespiratory parameter of an individual, comprising the steps of:

attaching at least two electrodes to the individual's body in a manner ensuring a low impedance contact between the electrodes and the individual's skin, and positioning the electrodes so that current which passes between the at least two electrodes flows between at least one arm or at least one leg to at least another arm or at least another leg of the individual;

passing an alternating current with a stable and constant amplitude through said at least two electrodes and at the same time, measuring the potential change as the result of the current flow, whereby an electrical bioimpedance measurement of the individual's body from the measured potential between the said at least two electrodes is obtained;

simultaneously separating an active component from said integral bioimpedance;

calculating the at least one cardiorespiratory parameter of said individual from the active component of said integral bioimpedance, using an empiric formula applicable to integral bioimpedance measurements, in such a manner so as to obtain a number of values of said at least one parameter for a number of cardiac cycles during a respiratory cycle, and calculating an average of said at least one parameter during a single respiratory cycle; and displaying the average cardiorespiratory parameters thus obtained.

The basic hemodynamic parameter Stroke Volume (SV) may be calculated according to the following equation:

$$SV = \frac{Hct_{corr.}}{K(shape*sex*age)} * \delta r \frac{H_{corr.}^2}{R} * \frac{\alpha+\beta}{\beta} * Kel * Kw * IB \quad (1)$$

where:

$Hct_{corr.}$ a correcting factor depending from Hematocrit, being $145+0.35(Hct-40)$;

Hct Hematocrit, obtained from the blood analysis of the individual;

K(shape*sex*age) a coefficient of the individual's body, being:

| men younger than 20 years old | women younger than 18 years old |
|---|---|
| $= 527.3 - (3.1 *$ | $= 587.6 - (2.9 *$ |
| (Actual Age $-20$)); | (Actual Age $-18$)); |
| men from 20 to 40 years old | women from 18 to 50 years old |
| $= 527.3$; | $= 587.6$; |
| men older than 40 years old | women older than 50 years old |
| $= 527.3 + (3.1 *$ | $= 587.6 + (2.9 *$ |
| (Actual Age $-40$)); | (Actual Age $-50$)); |

$\delta r/R$ the ratio characterizing the measured active bioimpedance component's change, $\delta r$, with respect to the individual's body resistance R $\delta r$ the amplitude value of the change of the individual's body basic resistance R on the anacrotic (systolic) portion of a cardiocycle.

R basic resistance of the individual's body during one cardiocycle.

$H_{corr.}$ the corrected height of the patient, given by:

$$H_{corr} = (H_{real} + 2) \text{ if } \frac{\text{legs length}}{\text{body length}} = 0.66 \pm 0.04 \quad (2)$$

or $$H_{corr} = (H_{real} - 2) \text{ if } \frac{\text{legs length}}{\text{body length}} = 0.54 \pm 0.04$$

or $$H_{corr} = (H_{real}) \text{ if } 0.62 \geq \frac{\text{legs length}}{\text{body length}} \geq 0.58$$

$\alpha+\beta$ duration of a cardiac cycle, being a sum of its anacrotic and catacrotic parts;

$\beta$ duration of the catacrotic part of a cardiac cycle;

Kel coefficient of electrolytic ions in the individual's blood, calculated based on the blood analysis and being given by:

a) for an individual exposed to a hemodialysis $$Kel = \frac{(Na^+ + K^+ + Mg^+ + Ca^+)(mmol/l)}{142 + 13 \text{ (mmol/l)}} \quad (3)$$

b) for other individuals $$Kel = \frac{(Na^+)(mmol/l)}{142 \text{ (mmol/l)}} \quad (4)$$

$K_w$ the weight coefficient, being Actual weight/Ideal weight* *(according to the International Tables of ideal weights)

IB Index Balance, reflecting ratio between the measured volume of extracellular fluids and the individual's proper volume of extracellular fluids. This is calculated on the basis of a formula for th "ideal content of body water", adapted from Kushner, R. T. et al., (*Amer. J. Clin. Nutr.*, 44:417–424, 1986):

$$IB = \frac{R \text{ individual's proper}}{R \text{ measured}} \quad (5)$$

where:

R measured—the individual's active (resistive) component of the bioimpedance measured either by tetrapolar mode, or by bipolar mode with correction to the individual's skin resistance.

R individual's proper is calculated according to the two following formulae:

$$\frac{0.42H^2}{0.47W - 8.30} \text{ for men} \quad (6)$$

$$\frac{0.42H^2}{0.37W - 4.96} \text{ for women}$$

where

H—the individual's height

W—the individual's weight

The above described novel equation (1) demonstrates that individual differences in bioimpedance of a specific human body can be considered by correcting the formula according to the particular features of the individual's body.

The electrodes may, in principle, be attached to any portion of the individual's extremities, add preferably to distal parts thereof.

The method in accordance with the invention can be carried out either in a bipolar or a tetrapolar mode. In accordance with a bipolar mode of carrying out the invention, at least two electrodes are utilized, wherein any electrode attached to an arm or a leg is used both for current injection and voltage measurement. In accordance with a tetrapolar mode of carrying out the invention, at least four electrodes are utilized; different electrodes are used for current injection than those which are used for voltage measurement. Thus, in accordance with the latter mode of the invention, the arm or leg under examination is typically fitted with two electrodes, the current injection being between a first pair of electrodes located each on a different arm or leg, and the voltage is measured by a second pair of electrodes, located on same, respective, arm or leg.

When performing the bipolar mode of the invention, two electrodes are usually utilized. Where two electrodes are being used they are typically attached, one to an arm arid the other to a contralateral leg. However, it is possible to determine the main cardiorespiratory parameters by attaching the two electrodes to the two arms of the individual, to the two legs, or to one arm and one semi-lateral leg. Although the attachment of one electrode to an arm and the other to a contralateral leg is preferred, the other mode of attachments may at times be used where an arm or a leg are diseased in a manner which avoids attachment and/or obtaining accurate or reliable readings.

In accordance with another embodiment of the bipolar mode of the invention, two electrodes connected to one another are attached to each of the individual's arms, and another two electrodes, again connected to one another, are attached to each of the individual's legs. In accordance with this embodiment, the current in injected in parallel between the two arms and the two legs and the voltage is simultaneously measured also between the two arms and the two legs.

All the electrode's placements described above for the bipolar mode may be applied also for the tetrapolar mode (the difference being in that rather than a single electrode at each site, there will be two such electrodes in accordance with the tetrapolar mode).

The skin resistance of an individual may differ from time to time and the different skin resistances may have an effect on the measured results. In order to measure skin resistance, in accordance with an embodiment of the invention, an auxiliary pair of current injecting electrodes is used in addition to the standard pair of current injecting electrodes applied in accordance with the bipolar mode described above, and constituting also the voltage measuring electrodes. The auxiliary current injecting electrodes are attached so that each one of the pair of such electrodes is placed at a certain distance, e.g. about 4 cms., away from the respective standard electrodes. For example, where the standard electrodes are placed one attached to an arm and the other attached to a contralateral leg, the auxiliary current injecting electrodes will be placed on the same arms and legs, a certain distance from the standard electrode pair. Typically, the auxiliary electrodes will be placed to be more distal than the standard electrodes.

In accordance with this embodiment (the skin resistance measuring embodiment) current will first be injected through the standard electrodes and voltage will be measured on the same standard electrodes. Then current will be injected through the auxiliary electrodes and voltage will be measured again between the standard electrodes, the difference in measured voltage being accountable for the skin resistance.

In other words, the standard measurement is made by utilizing the bipolar mode, but for the auxiliary measurement the tetrapolar mode is used, in which the electrodes utilizing the bipolar mode serve then for voltage measurement only. Thus in a skin resistance measurement, there will typically be a combination of the bipolar and tetrapolar modes.

The skin resistance in a combined bipolar/tetrapolar measurement mode as described above, is thus determined by the following formula:

$$R_s = R_1 - R_2 \quad (7)$$

wherein $R_s$—is the skin resistance, i.e. resistance between the current injection electrode and the skin in the bipolar mode, $R_1$—is the individual's resistance measured between two electrodes according to the bipolar mode, and $R_2$—is the resistance measured in the same individual when applying the tetrapolar mode.

When using the bipolar mode, the measured active component of the individual's bioimpedance, which forms a basis for the calculation of main cardiorespiratory parameters, constitutes $R_1$. Since the value of skin resistance $R_s$ may vary during the measurements, the value of the measured resistive component should be adjusted, so as to reduce the error of measurement.

Moreover, the skin resistance may have also a separate diagnostic significance.

The general approach in the art, for example that of Lukaski, et al., (*The American Journal of Clinical Nutrition*, 41:810–817, 1985) states that various configurations of electrode's placement (i.e., arm-leg, leg-leg, arm-arm) do not substantially affect results of whole body EBM measurements, more particularly, measurements of the resistive component R of the bioimpedance. However, when carrying out the method of the invention, it was found that results obtained at different electrodes' configurations may be somewhat different from one another, and therefore by comparison of such different results, it is possible to obtain information having a diagnostic significant.

For example, where the parameters are obtained by measuring between an individual's two arms (an "arm-arm" placement), the readings obtained are influenced primarily by the pulmonary circulatory system and functions of the individual's right ventricle. When the parameters are obtained by an "arm-leg" placement, the results will characterize a systemic circulation (represented mainly by the aorta) and thus will reflect functions of the individual's left ventricle.

As will be appreciated, in a healthy individual, the results obtained with the mentioned two electrode's placements (arm-arm and arm-leg) will be substantially the same. However, at different pathological situations, particularly where the individual has certain cardiorespiratory diseases, there will be a difference between the results obtained at the two electrode placements and such differences, possibly with the aid of additional measurement as will be detailed below, may be used to diagnose the cite and type of the disturbance.

The above-mentioned differences may be correctly detected and interpreted where the individual's extremities to which the electrodes are attached, do not have blood circulation problems. Thus, in order to allow proper interpretation of such results, errors which may be introduced by disturbances in the peripheral blood circulation, should be excluded. The following is an example of the sequences of steps to exclude such errors and to allow a preliminary functional diagnosis of such disturbances.

Step 1: Examination of the peripheral blood circulation

For examination of the peripheral circulation parameter P, represented by the following equation (6) and forming part of the equation (1) can be chosen:

$$P = \delta r \frac{H^2 \, corr}{R} * \frac{\alpha + \beta}{\beta} \quad (8)$$

Alternatively, or in addition, portions of the equation (8) may be used as parameters $P_1$, $P_2$ or $P_3$ represented by the following formulae (9–11):

$$P_1 = \frac{\delta r}{R} \quad (9)$$

$$P_2 = \frac{H^2 \, corr}{R} \quad (10)$$

$$P_3 = \frac{\alpha + \beta}{\beta} \quad (11)$$

The peripheral circulation, i.e. the circulation in the arms and legs is checked using the basic "leg-leg", "arm-arm", and "arm-leg" connectivity configurations together with an addition connectivity configurations, which include measurement between pairs of electrodes, one situated at a distal part of an arm or leg and the other on the shoulder or hip.

The readings of P and $P_1-P_3$ which are obtained using the "leg-leg" configuration are characteristic primarily of the individual's peripheral blood circulation (i.e., without the aorta and the pulmonary arteries). Where the above mentioned parameters obtained in a "leg-leg" electrode placement are substantially different from the ones obtained by the "arm-arm" and "arm-leg" placements, this may be indicative of peripheral circulatory problems, mainly such associated with an individual's legs.

In order to reveal a circulation related pathology in the leg, a pair of additional electrodes may be attached to the individual's hips, to provide EBM measurements between the distal pans of the leg and the hip for each leg. Values of P and $P_1$ to $P_3$ which are obtained for both legs, may then be compared to one another and with the values of the proper P, $P_1$, $P_2$ for the individual (i.e. values for these parameters which are obtained with R proper—see equation (5)).

A pathologic arm may be diagnosed in an analogous manner applying additional electrodes to the shoulders of the individual, obtaining readings of P and $P_1-P_3$, and processing thereof, in a similar manner as in the leg.

In order to measure the Stroke Volume parameter (SV), either one of the above-noted "arm-arm" and "leg-arm" connectivity configurations may be used. However, in order to allow derivation of left ventricle Stroke Volume and right ventricle Stroke Volume, a more complicated so called "arm-arm-leg" connectivity configuration is required to obtain a multi channel bioimpedance measurement, i.e., "arm-arm" and "arm-leg" measurements are typically performed by automatic multiplexing. In order to obtain such multi channel measurement, it is thus necessary that the two arms of the individual will be healthy and that the individual will have at least one healthy leg (it should be noted that conditions where individuals have arms with circulatory problems, are very rare).

In order to obtain measurements characterizing left ventricle and right ventricle functions, the method can then be accomplished according to Step 2 described below.

Step 2: Examination of left ventricle and right ventricle functions

If no pathology has been revealed in the peripheral circulation, the parameters (such as the Stroke Volume (SV) and the Index Balance (IB)), for the systemic circulation, and the ones for the pulmonary circulation, may be compared in order to define whether there is any pathology in the left or right ventricle's functions. This is based on the fact that various heart pathologies cause redistribution of the blood between the systemic and the pulmonary circulatory systems.

In general, when the value of SV measured in the "arm-arm" placement is substantially equal to that measured by the "arm-leg" placement, function of the left and right heart ventricles are considered to be in order. Imbalances may be caused by various reasons and can be classified as is suggested below.

For example, a temporary imbalance occurs whenever the right ventricle pumps more blood into the pulmonary blood vessels, than is removed therefrom by the left ventricle. Such a situation is a signal of the left ventricle heart failure (LVHF), which may be caused by various reasons, such as: impairment in the filling of the left ventricle (as in mitral stenosis); inability of the left ventricle to adequately empty itself during each contraction (as in heart failure caused by hypertension, coronary artery disease, aortic insufficiency or sortie stenosis, etc.). The excess blood may accumulate in the lungs even when the output of the left ventricle is normal or increased, but it is lagging behind that of the right ventricle, i.e. the left ventricle is unable to sufficiently increase its output to clear the lungs. Such a case may occur when a patient suffers from fever, anemia, beriberi, thyrotoxicosis, etc., where normal function of the left ventricle is imparted by the desease.

It is understood that if the SV value measured by the "arm-leg" electrode's placement (and predominantly characterizing functions of the left ventricle) is substantially less than the normal known SV value for the left ventricle, it indicates the left vetricle heart failure (LVHF). Moreover, when the SV value measured by the "arm-ten" electrode's placement (and predominantly characterizing functions of the left ventricle) is substantially lower than the SV value measured by the "arm-arm" electrodes placement, this may be an indication of at least one of the following:

1. Where such a discrepancy is additionally accomplished by increasing (above normal) of the IB parameter characterizing volume of the extracellular fluids in the individual's body, this may be an indication of a lung edema. Thereby, it is often possible to early diagnose a lung edema.
2. Where the IB value is normal, the discrepancy may be indicative of the existence of disturbances in the lung blood circulation.

According to a second aspect of the invention, there is provided a non-invasive medical device for accurately determining at least one cardiorespiratory parameter of the human body, said device comprising:

at least two electrodes, as electrical body integral bioimpedance measuring unit coupled to the electrodes and including a high stability amplitude alternative current source and an electronic circuit for automatic derivation of an active component of said integral bioimpedance; and a computer coupled to the electrical integral bioimpedance measuring unit and to a display means for calculating and displaying said at least one cardiorespiratory parameter from the active component of the integral bioimpedance.

BRIEF DESCRIPTION OF THE DRAWINGS

In order to understand the invention and to see how the same may be carried out in practice, some preferred embodiments will now be described, by way of non-limiting example only, with reference to the accompanying drawings, in which:

FIG. 1A is a block diagram showing functionally a measuring system according to the invention using four electrodes;

FIG. 1B is a schematic circuit diagram representing the system shown in FIG. 1A;

FIG. 1C is a block diagram showing functionally a measuring system according to the invention using two electrodes;

FIG. 1D is a schematic circuit diagram representing the system shown in FIG. 1C;

FIGS. 1E, 1F and 1G depict modifications of the system shown in FIG. 1C;

FIG. 1H illustrates the best mode of electrodes' placement suitable both for obtaining the main cardiorespiratory parameters according to the invention, and for diagnosing disturbances in the heart right and left ventricle functions and in the peripheral bleed circulation;

DETAILED DESCRIPTION OF PREFERRED EMBODIMENTS

Figure 2A:
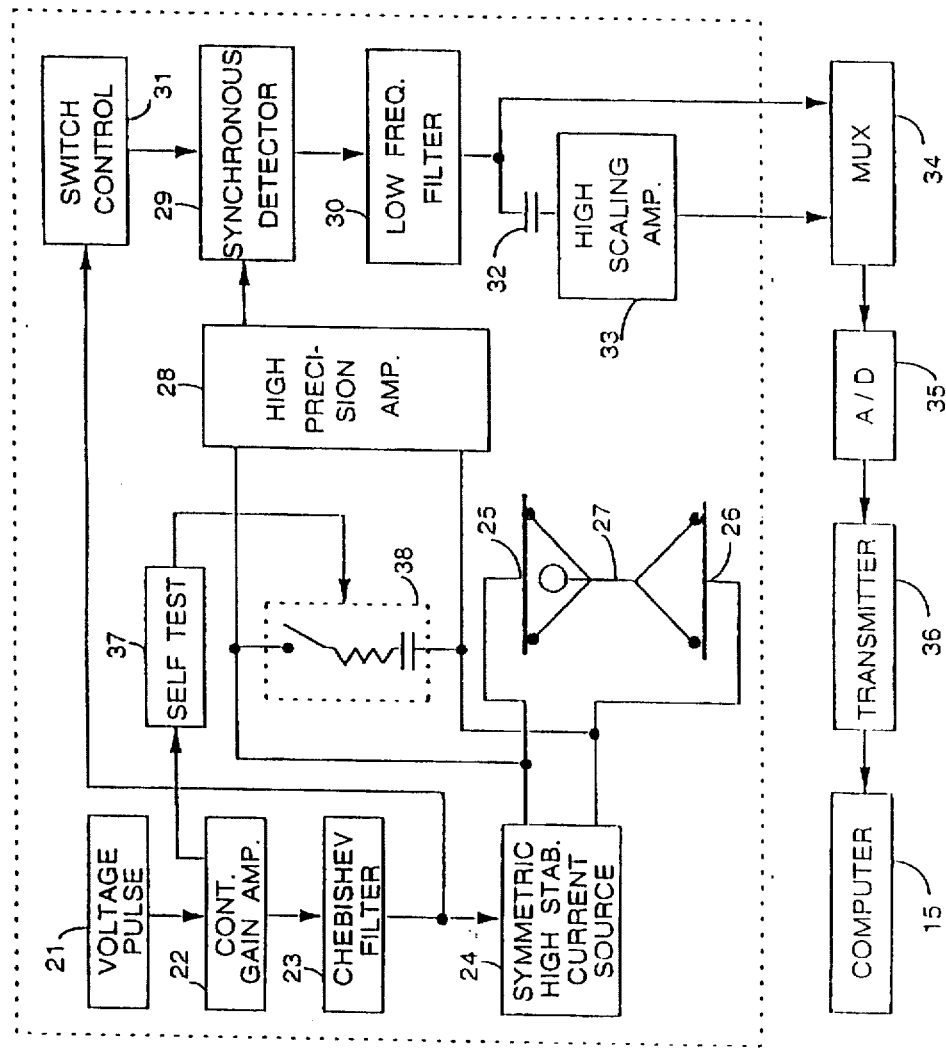
FIG. 2A is a block diagram showing schematically an electrical integral bioimpedance measuring system according to the invention.

FIGS. 1A and 1B show respectively a block-diagram of a non-invasive four-electrode system for automatic express determination of the main cardiorespiratory parameters of an individual 10 and an equivalent electrical circuit diagram of the individual 10.

Four electrodes 11, connected in two pairs, are applied to the distal parts of the arms and legs of the individual 10. An electrical integral bioimpedance measuring unit 12 delivers a high stability amplitude alternating current through a single channel 13, via the electrodes 11 to the individual 10. The integral impedance curve of the individual 10 is obtained from the same electrodes 11 and is transferred through the same single channel 13 to the measuring unit 12, which converts the integral impedance curve. The converted working signal is then transferred through a second single channel 14 to a computer 15, where cardiorespiratory parameters of the whole body and parameters concerning extracellular fluids of the whole body are calculated using empiric formulae.

Personal data characteristic of the individual 10 which is entered into the computer 15 via a keyboard (not shown) can also be taken into account when calculating the cardiorespiratory parameters. Typically, the personal data includes height, weight, age, sex, results of a blood test, identification index, etc. An output signal 14 from the electrical integral bioimpedance measuring unit 12 is fed to the computer 15 and stored in an internal table. Preliminary processing of the raw data is performed so as to derive a plethysmographic and rheographic curve, on the basis of which the respiratory cycle and heart beat complex indices (marks) are determined (the beginning of the anacrotic slope, the length of heart complexes' cycle, their maximum amplitude, e.g. by locating extremes of the curves, etc.). The area section under the initial impedance curve reflecting the phases of the fast and slow ejection of the blood during a cardiocycle is used for computing the main parameters. Based on this data and the individual's personal data, the parameters are determined using empiric formulae, such as those described below.

The computer 15 may be programmed to calculate a plurality of parameters based on the above definition of the Stroke Volume equation (1).

FIGS. 1C and 1D show respectively a block-diagram of a non-invasive two-electrode system for automatic express determination of the main cardiorespiratory parameters of a patient 10' and an equivalent electrical circuit diagram of the patient 10'.

A first electrode 11a is connected to the distal part of the left arm, and a second electrode 11b to the distal part of the patient's right leg. All the other elements of the system remain the same as the system described above and depicted in FIG. 1A.

It should be noted, that owing to the difference between the equivalent electric diagrams of the patient 10' used in the system shown in FIGS. 1B and 1D, the integral bioimpedance of the patient as measured by the system of FIG. 1C will be higher than that measured by the system according to FIG. 1A, as explained above. This enables at times to obtain a stronger initial obtained signal, thus improving the accuracy of the further electric transformations and calculations by the system.

Moreover, in this two-electrode configuration the current flow is mainly directed through the heart and the chest part of the patient's aorta, being the actual target for the measurements; and the current is less dissipated throughout the extremities and chest arteries. These two factors may improve the reliability of the measurements. This two-electrode configuration is also more patient-friendly than the four-electrode configuration and also enables a physician to make simultaneously some additional needed measurements, e.g. blood pressure measurements or provide treatment through the patient's second arm or leg, e.g. infusion.

Some other possible variants of the electrodes configurations are shown in FIGS. 1E to 1G. In each case, either two or four electrodes may be connected to the patient. In case of the former, the arrangement reduces to the bipolar system described above with reference to FIGS. 1C and 1D of the drawings. If the electrodes which are shown by dotted lines are also connected, then the arrangement yields a tetrapolar scheme in which two of the electrodes are active in injecting the current, whilst two of the electrodes are passive and measure the resultant signal.

Calculation of the cardiovascular parameters in this configuration needs specific corrections in comparison with hitherto-proposed calculations for the four-electrode system. These corrections may require means of adjusting of the empiric coefficients as defined above.

Reference is now made to FIG. 1H illustrating the best mode of electrodes' placement suitable both for obtaining the main cardiorespiratory parameters according to the invention, and for diagnosing of disturbances in the heart right and left ventricle functions and in the periphery blood circulation.

To the distal parts of all the individual's two arms and two legs, four electrodes are attached which are marked "a" in the figure, for measurement by the bipolar mode. Another pair of current injecting electrodes, marked "b", are attached to one arm and one leg of the individual, typically the right arm and the right leg. These electrodes which are preferably placed, as shown in the figure, in a more peripheral position than the "a" electrodes, are used to measure the skin resistance, $R_s$, by the combined bipolar/tetrapolar mode described above. Four additional and optional electrodes, marked "c" are attached to the shoulders and to the hips of the individual, which are used for the purpose of obtaining information of the peripheral circulation, the blood circulation in the arms and legs. This electrode configuration thus allows derivation of a complete set of cardiorespiratory parameters, as described above, and also functional circulatory parameters, distribution of the extracellular fluid throughout the body, and diagnosis of disturbances in the blood circulation and in the heart right and left ventricle functions.

FIG. 2A is a block-diagram of the electrical integral bioimpedance measuring unit depicted as 12 in FIGS. 1A and 1C. It should first be noted, that the human body behaves, from an electrical point of view, as an RC (resistance-capacitance) impedance. The operation of the unit 12 described below clarifies the method suggested according to the present invention.

The electrical integral bioimpedance measuring unit 12 comprises a voltage pulse generator 21, producing 30 KHz rectangular pulses. These pulses are directed to a controllable gain amplifier 22 an outlet of which is connected to a Chebishev filter 13 for convening the signal to a sinusoidal form. The outlet of the filter 23 is connected to an inlet of a symmetric high stability amplitude alternating current source 24. The high stability amplitude current maintained at the outlets of the current source 24, is applied through two pairs of electrodes 25, 26 to the human body 27.

The recorded voltage signal, proportional to the human body impedance Z, i.e. an integral bioimpedance) is transferred from the electrodes and 26 to a high precision amplifier 28, whose outlet is fed to a first input of a synchronous detector 29. The synchronous detector 29 has two functions: first, it rectifies the obtained integral bioimpedance, and secondly, it provides simultaneous derivation of the active component of the integral bioimpedance voltage vector. This component is directly proportional to the resistive component of the lead (resistance of the blood system as stated by Tishcenko).

The second function is provided with the aid of a switch controlling scheme 31, connected at an inlet thereof to an outlet of the filter 23, and at an outlet thereof to a second input of the synchronous detector 29.

The linear behavior of the synchronous detector 29 simplifies the calibration process and reduces it to a one time, initial adjustment (instead of a per cycle calibration).

A low frequency filter 30 being, for example, a low pass Bessel filter, is connected to an outlet of the synchronous detector 29. The low-pass filter 30 cuts off high frequency components, for example above 32 KHz, and delivers a working signal. The working signal, being the active bio-impedance component, is then divided by a capacitor 32 into a direct current (DC) component and an alternating current (AC) component. The AC component is amplified by a high scaling amplifier 33 and is fed together with the DC component to respective inlets of a multiplexer 34. An output of the multiplexer 34 is connected to an analog-to-digital (A/D) converter 35, which is connected to the computer 15 (FIGS. 1A and 1C) through a transmitter 36.

Figure 2B:
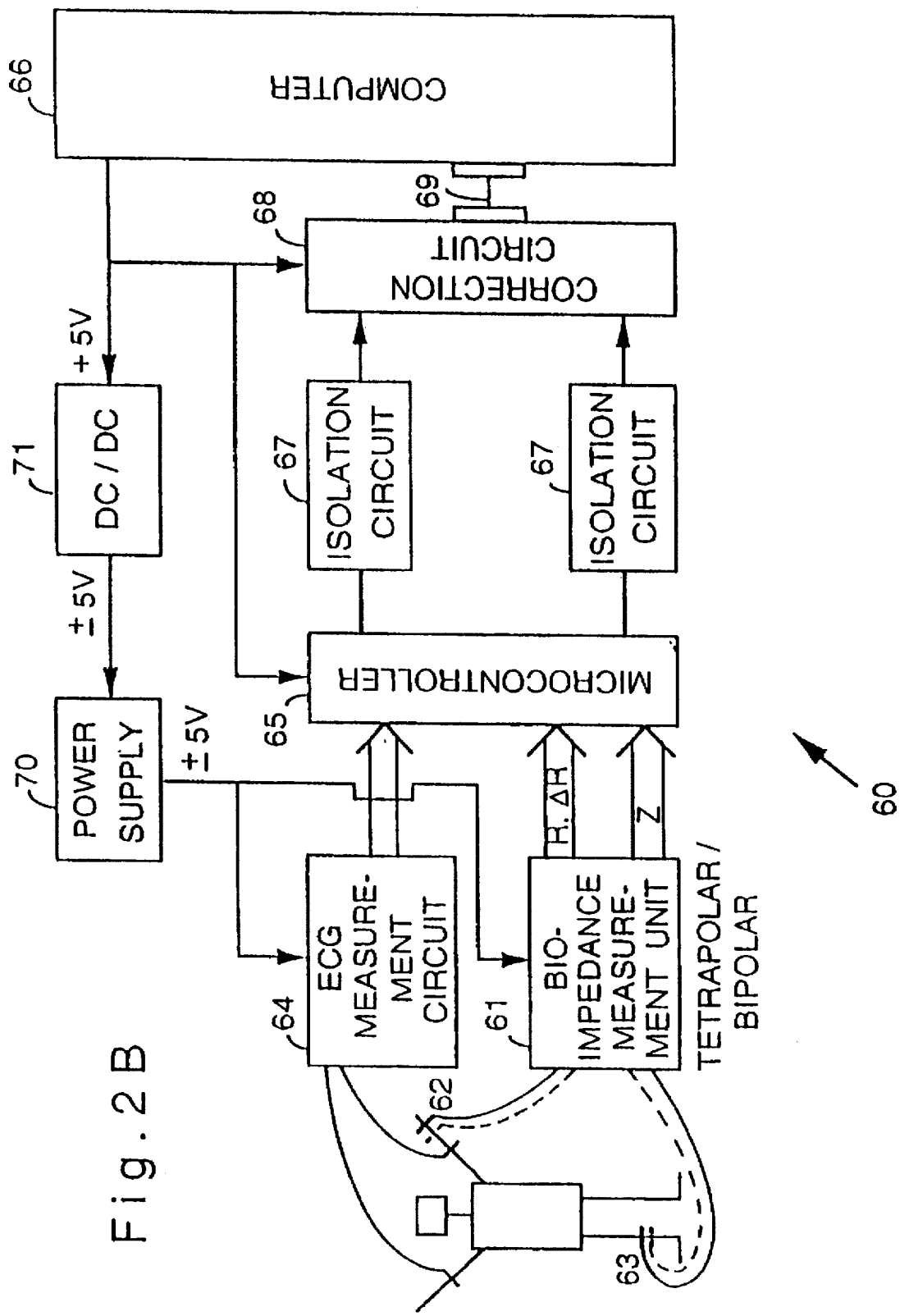
FIG. 2B is a block diagram showing a modification of the instrument shown in FIG. 2A.

Also provided is a self-testing block for testing the unit before starting the measurements comprising a control unit 37 connected to the second outlet of the controllable gain amplifier 22 and a simulating impedance circuit 38 connected across the patient's body FIG. 2B is a block-diagram of a unit 60 which is a modification of that described above with reference to FIG. 2A. The Bioimpedance Measuring Unit which is depicted in FIG. 2A within a dashed line, is unit 61 in FIG. 2B. It should be noted, however, that two electrodes 62 and 63 are now applied to two of the patient's extremities, shown outside the Bioimpedance Measuring Unit 61 as opposed to the four electrodes shown in FIG. 2A. Two additional ECG electrodes are applied to the arms of the patient and connected to an ECG measurement circuit 64.

A micro-controller 65 (such as model 80196KC manufactured by Intel®) combining the functions of the A/D converter and a microprocessor, is provided for processing in real time a curve obtained from the ECG circuit 64, together with the curve obtained from the Bioimpedance Measuring Unit 61 and being a composition of a direct "R" and an alternating "δR" components of an active bioimpedance component. Additionally, the micro-controller 65 receives the initial complete bioimpedance curve from the Bioimpedance Measuring Unit 61 (more particularly from the output of the High Precision Amplifier 28 shown in FIG. 2A). When processing both the initial bioimpedance curve and the curve of the active bioimpedance component, the micro-controller 65 and a computer 66 (such as a note-book computer) continuously calculate a capacitance of the electric circuit of the human body. The value of the capacitance of the human body can be calculated by the formula:

$$Z = R - \frac{j}{\omega C}$$

and continuously checked.

An excess of the capacitance over a predetermined threshold, or oscillation of the capacitance indicates degradation of the contacts between the electrodes and the patient's skin. In such case, an appropriate alarm is activated under control of the computer 66. The outputs of the microcontroller 65 are connected to the computer 66 via isolation circuits 67 (such as opto-isolators MOC 8080, Motorola®) providing electrical protection of the patient from a random voltage, via a correction circuit 68 (such as the driver RS232C) and an appropriate RS232C cable 69. The correction circuit 68 and the micro-controller 65 are supplied with electrical voltage of +5V from the computer 66. The voltage ±5V from the power supply 70 is convened to +5V by a DC/DC converter 71. The DC/DC converter 71 also performs a function of an isolation circuit. The power supply unit 70 provides the blocks of the instrument 60 with electrical power of ±5V.

Figure 3A:
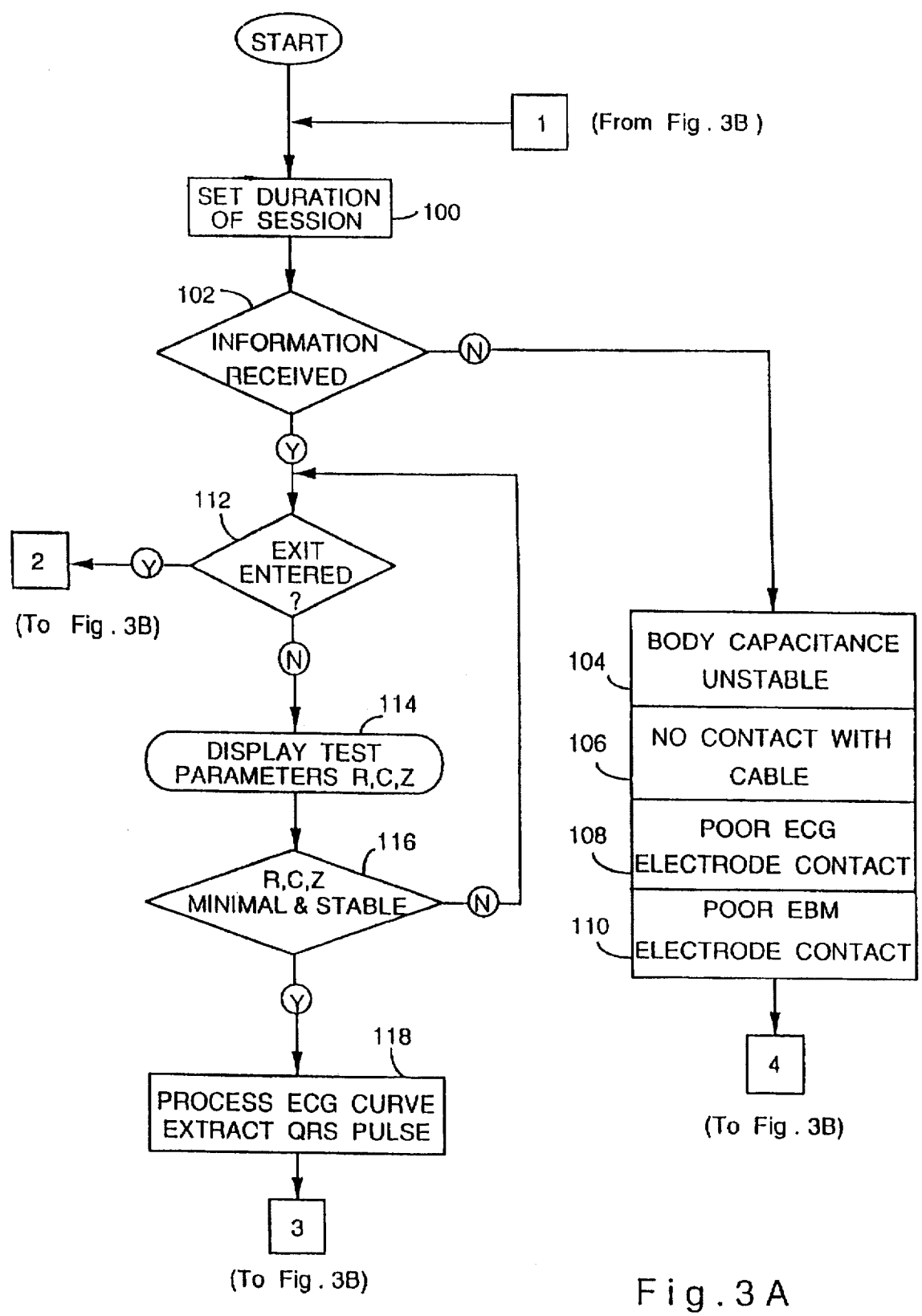
FIGS. 3A and 3B are a flowchart showing the principal steps in a method for using the measuring system according to the invention.
Figure 3B:
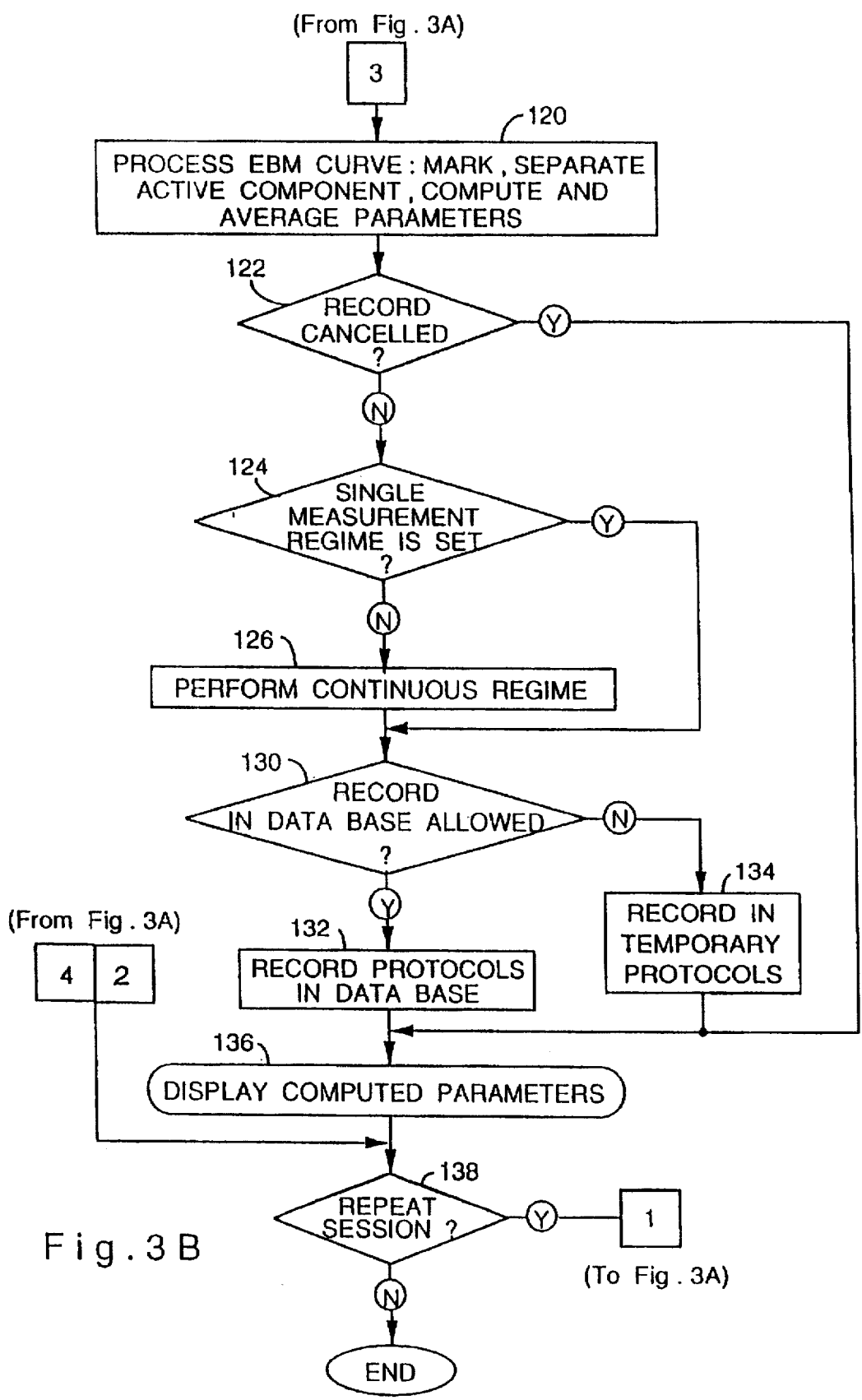

FIGS. 3A and 3B shows a flow diagram of an algorithm in accordance with which the system functions.

At step 100 the system is switched on, and the duration of the monitoring session is chosen. The duration of the monitoring session can be defined as a duration of an initial bioimpedance curve section intended for an averaged calculation of the necessary parameters, and can be chosen in the range of about 10 to 30 sec.

At step 102 a check is performed in order to determine whether the information from the Bioimpedance Measurement Unit 61 is obtained on the display. If not, the reason should be detected and indicated by at least one of the following test blocks:

Block 104 The impedance between electrodes and the skin is not stable;

Block 106 There is no contact in the cable RS232C;

Block 108 The ECG electrodes contact is poor;

Block 110 A poor contact of the bioimpedance measuring electrodes.

After overcoming the reason for the malfunction, the cycle should be started again (returning to step 102). If no exit command were keyed by an operator (block 112), the digital test readings of R (active impedance), C (capacitance), and Z (complete impedance) will be displayed in real time on the display (step 114).

When these parameters are stabilized (step 116), the next procedure is started wherein the QRS pulse is derived from the ECG curve (step 118) for marking the bioimpedance curve.

Step 120 represents the processes of marking of the bioimpedance curve by the marks obtained at step 118, further processing of the rheographic information and computing the main cardiorespiratory parameters being based on the average data obtained during a respiration cycle.

If a record of the computed parameters is not aborted at step 122, the parameters should be stored in the computer. The parameters in the system can be computed either in a regime of a single measurement (step 124), or in a continuous regime (step 126).

The computed parameters may be stored in the computer in one of the following two ways: the values of the parameters can be either entered into a data base of the patient in the computer (step 132), or the parameters can be written down as a temporary protocol in the computer (step 134). At step 130 it is decided whether or not the data base should be used for the record of the computed parameters.

When the single monitoring session is finished, a plurality of the computed parameters are indicated on the display (step 136). At step 138 there is defined whether or not to repeat the measurements. The order to repeat the measurements can be entered either manually by the operator, or automatically, if the continuous regime were chosen. If such an order is received, another monitoring session will be started, and additional readings of the parameters will be recorded. If the measurements are not to be repeated, the process will be stopped at step 140.

Figure 4:
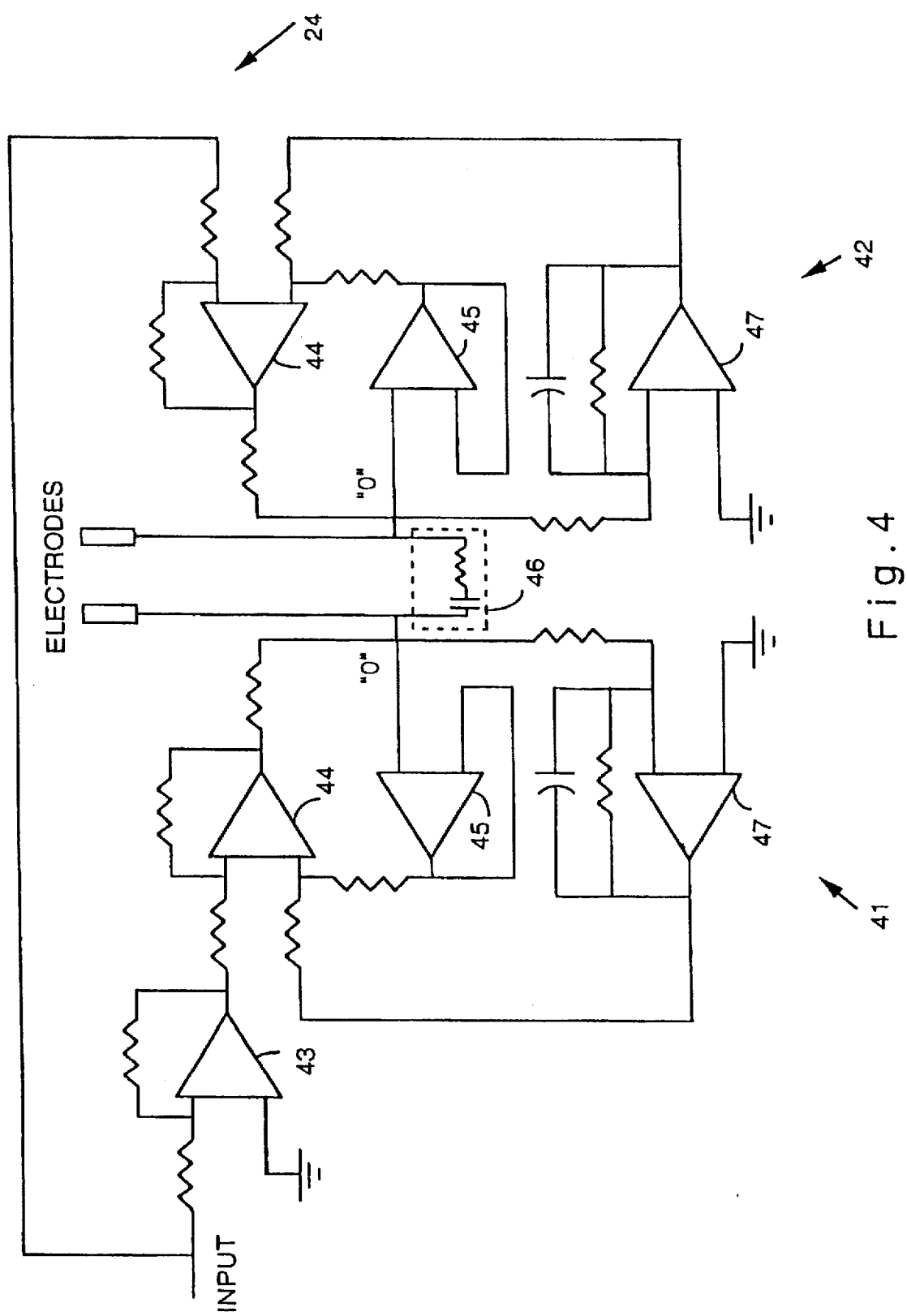
FIG. 4 is an electrical circuit diagram of the high stability amplitude alternative current source shown in FIG. 2A.

FIG. 4 shows an electrical scheme of the source of the high stability amplitude alternative current across an RC load. The current source 24 has a symmetric structure in order to minimize errors and noise appearing in the output signal. The second feature is its high stability ($10^{-5}$ to $10^{-7}$). The variations in the resistance, due to heartbeat and respiration cycles, are in the range of $10^{-3}$ of the total value. In order to make the measurements of these variations reliable, the stability of this circuit has to be at least two orders of magnitude greater. The current source 24 may, for example, deliver to the patient's body a current of 1 to 2 mA, at a frequency of 32 to 100 kHz.

The high stability amplitude alternative current source 24 comprises first and second symmetric current sources 41 and 42, in order to minimize errors appearing in the output signal. The two symmetric current sources 41 and 42 are connected to the voltage pulse generator 21 through the amplifier 22 and filter 23 (see FIG. 22A). The input point is shown as "input" in FIG. 4. The first current source. 41 is connected to the "input" through an inverter 43, and the second symmetric current source 42 is connected to the "input" directly.

The first current source 41 stabilizes the positive half-wave alternating voltage input, and the second current source 41 stabilizes the negative half-wave alternating voltage input. Each of the symmetric current sources 41 and 42 comprises three high precision operational amplifiers in conjunction with associated circuitry. The first operational amplifier 44, having a high output resistance, is fed with the alternating signal from the "input" point at the inverting inlet. A positive feedback is formed on the amplifier 44 by a second high precision, high speed operational amplifier 45. The first and second operational amplifiers 44, 45 stabilize the alternating current, passing over the RC load 46. The outlet of the first operational amplifier 44 and the non-inverting inlet of the second operational amplifier 45 form a zero point "0".

Owing to the high output resistance of any current source, stray currents or an asymmetric input voltage may deter the current source from a operating. In order to prevent this, the third operational amplifier 47, in conjunction with its appropriate circuitry, is connected at its inverting inlet to the zero point "0", and at its outlet to the non-inverting inlet of the first operational amplifier 44. The operational amplifier 47 provides a zero voltage DC level at the zero point "0", thus maintaining the current source in correct working condition. The load 46, being a human body, is connected to two symmetric zero points of the two symmetric current sources 41 and 42.

Figure 5:
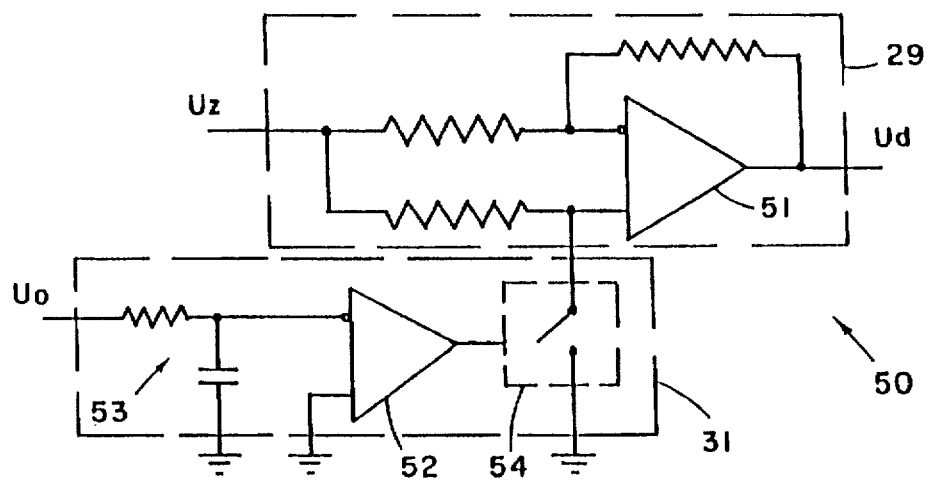
FIG. 5 is an electrical circuit diagram for achieving automatic separation of the active component from the integral bioimpedance.
Figure 6:
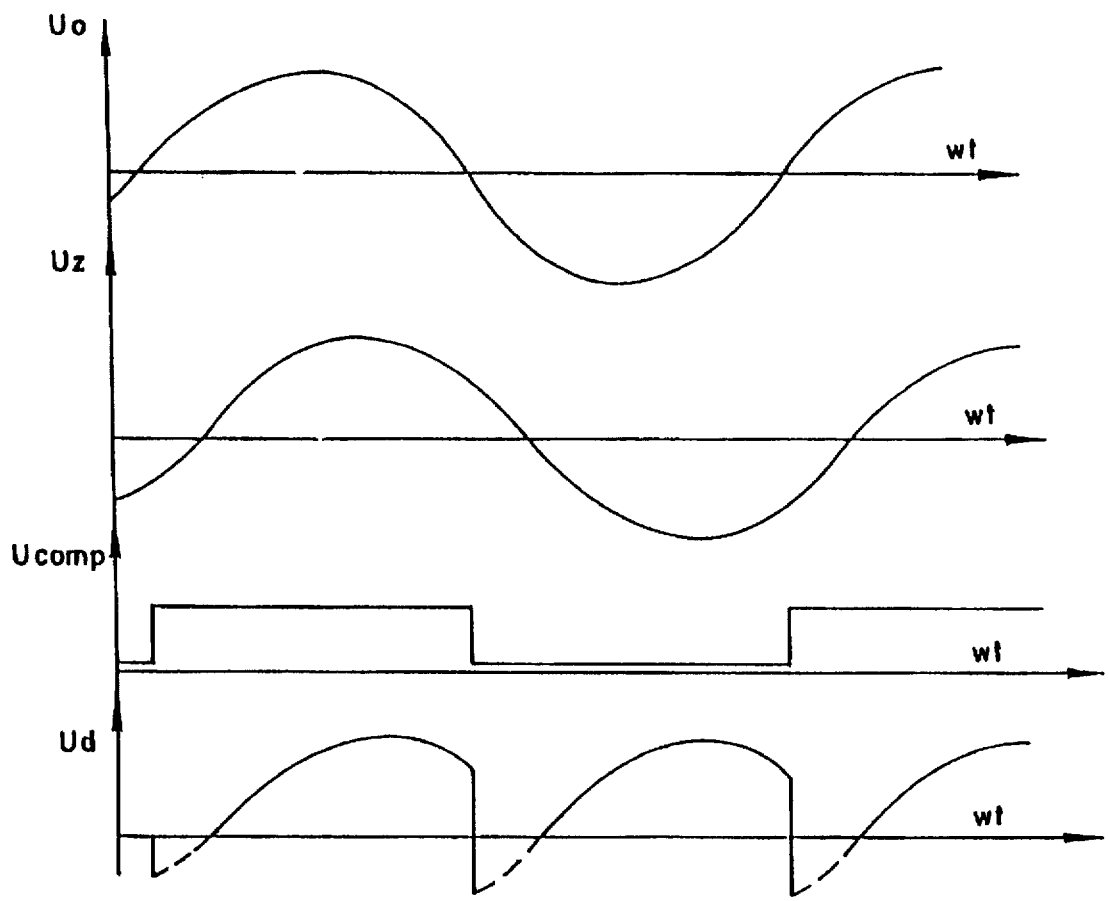
FIG. 6 is a timing diagram relating to operation of the circuit shown in FIG. 5.

FIGS. 5 and 6 show respectively the electronic circuit 50 for automatic derivation of the active component from the integral bioimpedance, and a time diagram describing the circuit's operation. The circuit is constituted by the synchronous-detector 29, associated with the switch controlling scheme 31 in FIG. 2A.

The circuit 50 comprises first and second operational amplifiers 51 and 52, respectively. The first operational amplifier 51 is connected at its inlets to the high precision amplifier 18 (see FIG. 2A). The second operational amplifier 52, functioning as a comparator, is connected at its inverting inlet to the outlet of the filter 23 (FIG. 2A) through an RC timing circuit 53. An outlet of the second operational amplifier 52 is connected to the non-inverting inlet of the first operational amplifier 51 through an electronic switch 54. The RC timing circuit 53 is intended to remove a delay in the triggering of the comparator 52 and the switch 54.

The electronic circuit 50 operates as follows. An alternating voltage $U_z$ from the outlets of the high precision amplifier 28 is applied to the both inlets of the first operational amplifier 51. The voltage $U_z$ is proportional to the voltage appearing across load constituted by the human body and represents its bioimpedance.

An alternating voltage $U_o$, from the outlet of the filter 23 is applied to one inlet of the comparator 51 through the RC timing circuit 53. Owing to the fact, that the voltage $U_o$ activates the high stability amplitude alternative current source 24, this voltage is proportional to the current $I_o$, passing through the human body load.

It can be seen on the timing diagram, that the $U_z$ curve is delayed relative to the $U_o$ curve; the delay being predetermined by the reactive component of the human body load. If $U_o$ becomes positive, the comparator 52 will immediately turn off the switch 54 (see the $U_{comp}$ curve), and a voltage will appear on the outlet of the amplifier 51 whose magnitude is given by:

$$U_d = K * U_z$$

where:

K is an amplifying coefficient.

If $U_o$ becomes negative, the comparator immediately operates the switch 54, and the amplifier 51 inverts the input voltage, whereupon the output voltage will be:

$$U_d = -K * U_z$$

Hence, the scheme described accomplishes detection of the input voltage $U_z$. The $U_d$ curve has positive sections, which can characterize the active component of the $U_z$ voltage curve by their duration and amplitude.

The positive $U_d$ voltage is filtered by the low frequency filter 30 (FIG. 2A). At the outlet of the filter 30 an alternating voltage $U_f$ is created, equal to the average value of the $U_d$ voltage. Voltage $U_f$ can be described by the following equations:

$$U_f = \frac{(2I_m * K * Z)}{T} * \int_0^{\frac{T}{2}} \sin(\omega t + \phi) dt$$

$$= (I_o * Z * K) \frac{1}{T} \cos\phi$$

where:

$I_m$ is the amplitude of the current passing through the load;

K is the amplifying coefficient=$U_d/U_z$;

$\omega$ is the angular frequency;

$\phi$ is the delay angle between the current and voltage curves;

$$\tan\phi = \frac{1}{\omega CR}$$

Z the impedance of the load being given by:

$$Z = \frac{R}{\cos\phi}$$

$$= \sqrt{R^2 + \left(\frac{1}{\omega C}\right)^2}$$

T is the period of the sinusoidal signal.
Using all these data it may be shown that:

$$U_f = \frac{R}{T} (I_m * K)$$

Hence, the voltage $U_f$, appearing on the outlet of the filter 30 is proportional to the active component R of the bioimpedance of the human body.

It has been shown that the method according to the invention comprises applying the electrodes according to either a bipolar or tetrapolar system. In either case, a preliminary connection of four electrodes may be effected to the respective distal pans of the human extremities, whereafter the integral impedance is preliminarily measured between each pair of electrodes placed on each arm and leg. Determination of the main cardiorespiratory parameters of the human body is made in accordance with which pair of electrodes is characterized by the lowest integral impedance.

In accordance with one embodiment, the method according to the invention further includes a computerized calculation of parameters concerning extracellular fluids of the patient's body, the calculations being based on measurements accomplished at two different current frequencies.

It should further be noted that the method according to the invention may also be employed for revealing the pathological extremities, where arterial blood circulation defects occur or another pathological defect takes place.

Moreover, if both of the upper extremities are under treatment or have associated therewith pathological defects (thrombophlebitis, tremor, oedema), or if the patient needs to be monitored for a long period of time, or has to have his arms free for other types of treatment or for required physical exercises, other arrangements of the electrodes' connection can be effected, especially for measuring of cardia-parameters.

In the preferred embodiment a plurality of such parameters are calculated by said method, including hemodynamic parameters such as Stroke Volume, Systolic Index, Pulse Rate, Cardiac Output, Heart Index, Reserve Index, Total Resistance Index, Index of Tone Stabilization; and respiratory parameters such as Rate of Respiration, Index of Respiration changes, Index of Respiration Intensiveness, Index of Hemodynamic Security; arid additional parameters, such as Index of Respiratory Duration and Index of Tidal Respiratory Volume.

In yet a further embodiment, a plurality of parameters characterizing extracellular fluids of the human body are calculated, such as Volume of Extracellular Fluids of the whole patient's body and Index of Fluid Balance of the whole body.

While the present invention has been described with the reference to the attached drawings, it should be appreciated, that other embodiments of the described system and its elements can be suggested and should be considered as part of the invention.

What is claimed is:

1. A method for determining at least one main cardiorespiratory parameter of an individual, the method comprising the steps of:

attaching at least two electrodes to the body of an individual and providing a low impedance contact between the electrodes and a skin of the individual, and positioning the electrodes on at least one arm or at least one leg and at least another arm or at least another leg of the individual to enable current to pass between said at least two electrodes on said at least one arm or at least one leg to at least another arm or at least another leg of the individual;

passing an alternating current with a stable and constant amplitude through said at least two electrodes;

measuring, while passing said alternating current, a potential change as the result of a current flow to obtain a measurement of an electrical integral bioimpedance of the body of the individual from a measured potential between said at least two electrodes;

simultaneously separating an active component of the integral bioimpedance from measured integral bioimpedance;

calculating at least one of a cardio parameter and a respiratory parameter of the individual from the active component of said integral bioimpedance, using a semi-empiric formula applicable to integral bioimpedance measurements to obtain a number of values of said at least one parameter for a number of cardiac cycles during a respiratory cycle, and calculating an average of said at least one parameter during a single respiratory cycle; and displaying said average of said at least one parameter thus obtained.

2. The method according to claim 1, wherein said cardiac parameter comprises a Stroke Volume (SV) parameter calculated substantially according to the following equation:

$$SV = \frac{Hct_{corr.}}{K(shape*sex*age)} * \delta r \frac{H_{corr.}^2}{R} * \frac{\alpha+\beta}{\beta} * Kel * Kw * IB$$

where:

$Hct_{corr.}$ is a correcting factor depending from hematocrit, being 145+0.35 (Hct−40);

Hct is the hematocrit, obtained from analysis of the individual's blood;

K(shape*sex*age) is a coefficient of the individual's body, being:
527.3−(3.1*(Actual Age−20)), for men younger than 20 years old;
527.3, for men from 20 to 40 years old;
527.3+(3.1*(Actual Age−40)), for men older than 40 years old;
587.6−(2.9*(Actual Age−18)), for women younger than 18 years old;
587.6, for women from 18 to 50 years old;
587.6+(2.9*(Actual Age−50)), for women older than 50 years old;

δr is the amplitude value of the change of the individual's basic body resistance R at the anacrotic (systolic) portion of a cardiac cycle;

R is the individual average basic body resistance during one cardiac cycle;

$H_{corr.}$ is a corrected height of the individual, given by:

$$H_{corr} = (H_{real} + 2) \text{ if } \frac{\text{legs length}}{\text{body length}} = 0.66 \pm 0.04$$

or $$H_{corr} = (H_{real} - 2) \text{ if } \frac{\text{legs length}}{\text{body length}} = 0.54 \pm 0.04$$

or $$H_{corr} = (H_{real}) \text{ if } 0.62 \geq \frac{\text{legs length}}{\text{body length}} \geq 0.58$$

α+β is duration of a cardiac cycle, being a sum of its anacrotic and catacrotic portion;

β is duration of the catacrotic portion of a cardiac cycle;

Kel is a coefficient dependent on ion concentration in the individual's blood plasma, calculated based on the blood analysis and being given by:

a) for an individual exposed to a hemodialysis Kel=sum of the blood concentrations at $$\frac{Na^+ + K^+ + Mg^+ + Ca^+}{142 + 13}$$

b) for other individuals

Kel=blood concentration of $Na^+/142$;

$K_w$ is a weight coefficient, being a ratio Actual weight/Ideal weight where Ideal weight being obtained from International Tables of ideal weights;

IB is an Index Balance, reflecting ratio between the measured volume of extracellular fluids and the individual's proper volume of extracellular fluids.

3. A method according to claim 2, wherein the Index Balance is calculated based on the following formula:

$$R_{ind.prop}/R_{measured}$$

where

R measured is the measured resistive component of the individual's bioimpedance, not including the individual's skin resistance;

$R_{ind.prop}$ is a proper value of the resistive component of the individual's bioimpedance being calculated according to the two following formulae:

$$\frac{0.42H^2}{0.47W - 8.30} \text{ for men}$$

$$\frac{0.42H^2}{0.37W - 4.96} \text{ for women}$$

where

H is the individual's height, and

W is the individual's actual weight.

4. The method according to claim 3, further comprising a preliminary step of examination of a peripheral blood circulation of the individual, said preliminary step including:

measuring at least one of parameters P, $P_1$, $P_2$ or $P_3$ between the individual's two arms having an arm-arm electrode attachment, between the individual's arm and leg having an arm-leg electrode attachment, and between the individual's two legs having an leg-leg electrode attachment; said parameters being calculated substantially by the following formulae:

$$P = \delta r \frac{H^2 \, corr}{R \, \text{measured}} * \frac{\alpha + \beta}{\beta}$$

$$P_1 = \frac{\delta r}{R \, \text{measured}}$$

$$P_2 = \frac{H^2 \, corr}{R \, \text{measured}}$$

$$P_3 = \frac{\alpha + \beta}{\beta} ,$$

comparing readings obtained in said leg-leg electrode attachment with readings obtained in said arm-arm and said arm-leg electrode attachment, and diagnosing peripheral circulatory disturbances at least in one of the legs of the individual based on a difference in readings obtained in the leg-leg electrode attachment compared to other attachments.

5. The method according to claim 4, wherein said preliminary step of examination of the peripheral blood circulation comprises:

applying a pair of additional electrodes to two hips of the individual, providing measurements of at least one of the parameters P, $P_1$ or $P_2$ between a distal part of each leg and a corresponding hip;

obtaining for each leg values of proper parameters $P_{proper}$, $P_{1prop}$ or $P_{2prop}$ for the individual, calculated according to the following formulae:

$$P_{prop} = \delta \frac{H^2 \, corr}{R_{ind,prop}} * \frac{\alpha + \beta}{\beta}$$

$$P_{1prop} = \frac{\delta r}{R_{ind,prop}}$$

$$P_{2prop} = \frac{H^2 \, corr}{R_{ind,prop}} ,$$

comparing the readings of at least one of the parameters P, $P_1$ or $P_2$ with the readings of the proper parameters $P_{prop}$, $P_{1prop}$ or $P_{2prop}$ for each leg, respectively, and defining a pathologic leg if the readings related to a leg substantially differ from the proper parameters, and excluding said pathologic leg from the electrode attachment chosen for determining the main cardiorespiratory parameters.

6. The method according to claim 5, wherein the Stroke Volume (SV) parameter is measured both for the arm-arm electrode attachment, and for the arm-leg electrode attachment, the two arms and the leg chosen for measurement having no disturbance in blood circulation; and wherein the two measurements are compared to each other; and and wherein a left ventricle heart failure is diagnosed where the SV value measured in the arm-arm electrode attachment substantially exceeds the SV value measured in the arm-leg electrode attachment.

7. The method according to claim 6, further comprising measuring Index Balance (IB) parameter;

diagnosing lung edema where the SV value measured in the arm-arm electrode attachment substantially differs from the SV value measured in the arm-leg electrode attachment, and the IB parameter is substantially higher than 1; and diagnosing problems in lung blood circulation where the SV value measured in the arm-arm electrode attachment substantially exceeds the SV value measured in the arm-leg electrode attachment, and the IB equals to about 1.

8. The method according to claim 3, comprising applying four additional electrodes, one to each of shoulders and hips of the individual, and a preliminary step of revealing disturbances in a peripheral blood circulation of the individual; said preliminary step including determining of at least one of parameters P, $P_1$ or $P_2$ between a distal part of each of the arms and legs and a corresponding additional electrode; said parameters being calculated substantially by the following formulae:

$$P = \delta r \frac{H^2 \, corr}{R \, \text{measured}} * \frac{\alpha + \beta}{\beta}$$

$$P_1 = \frac{\delta r}{R \, \text{measured}}$$

$$P_2 = \frac{H^2 \, corr}{R \, \text{measured}} ;$$

obtaining for each arm and leg values of proper parameters $P_{prop}$, $P_{1prop}$ or $P_{2prop}$ of the individual values calculated substantially according to the following formulae:

$$P_{prop} = \delta \frac{H^2 \, corr}{R_{ind,prop}} * \frac{\alpha + \beta}{\beta}$$

$$P_{1prop} = \frac{\delta r}{R_{ind,prop}}$$

$$P_{2prop} = \frac{H^2 \, corr}{R_{ind,prop}} ;$$

comparing at least one of the parameters P, $P_1$ or $P_2$ with a corresponding proper parameter $P_{prop}$, $P_{1prop}$ or $P_{2prop}$ for each arm and leg;

and defining at least one pathologic arm or leg if the readings of the parameters P, $P_1$ or $P_2$ related to said at least one arm or leg substantially differ from the values of the corresponding proper parameters $P_{prop}$, $P_{1prop}$ or $P_{2prop}$, and excluding said at least one pathologic arm or leg from the electrode attachment chosen for determining the main cardiorespiratory parameters.

9. The method according to claim 8, said step of measuring the Stroke Volume (SV) parameter including measuring the Stroke Volume (SV) both for the arm-arm electrode attachment, and for the arm-leg electrode attachment, the two arms and the leg chosen for measurement having no disturbance in blood circulation; comparing the two measurements to each other; and wherein a left ventricle heart failure is diagnosed where the SV value measured in the arm-arm electrode attachment substantially exceeds the SV value measured in the arm-leg electrode attachment.

10. The method according to claim 1, said attaching step comprising attaching the electrodes to distal parts of the arms and legs of the individual.

11. The method according to claim 1, wherein the method is carried out in a bipolar mode, and said attaching step comprises attaching said at least two electrodes to the body of the individual with each electrode being used for both said passing current step and said measuring step.

12. The method according to claim 1, wherein the method is carried out in a tetrapolar mode, and said attaching step comprises attaching at least four electrodes to the body of the individual, of which at least two electrodes are used for said passing current step and at least two other different electrodes are used for said measuring step.

13. The method according to claim 12, said attaching step comprising attaching one of a first pair of electrodes and a second pair of electrodes to one arm or leg and another one of said first and second pair of electrodes to another arm or leg, passing the current between the first pair of electrodes, each electrode of the first pair being located on a different arm or leg and measuring the potential between the second pair of electrodes, different from that of the first.

14. The method according to claim 1, wherein said attaching step comprises:

attaching first basic pair of electrodes to the individual, by attaching one electrode of said pair on one arm or leg and another electrode of said pair on another arm or leg; and attaching a pair of auxiliary electrodes by attaching each auxiliary electrode to one of the arms or legs to which the basic pair of electrodes are attached and positioning the auxiliary electrodes on a more distal portion of the arms or legs than the basic pair;

said measuring step comprises:

measuring impedance comprising a first step in which current is passed and potential is measured using the basic pair of electrodes, and a second step wherein current is passed through the auxiliary electrodes and potential measured through the basic electrodes, in a tetrapolar measurement mode;

calculating a difference between the potential measured in the first step and the potential measured in the second step to calculate resistance of the skin of the individual from said difference; and continuously reducing the resistance of the skin of the individual in accordance with a value of said active component of the integral bioimpedance of the individual.

15. A non-invasive medical system for accurately determining at least one cardiorespiratory parameter of the human body, the system comprising:

at last two electrodes, an electrical integral bioimpedance measuring unit for measuring integral bioimpedance of a human body, coupled to the electrodes and including a high stability amplitude alternating current source and an electronic circuit for automatic derivation of an active component of the integral bioimpedance; and a computer coupled to the electrical integral bioimpedance measuring unit for calculating an average value measured cardio parameter or a respiratory parameter of the individual, the average value being of a number of values of said parameter for a number of cardiac cycles during a respiratory cycle, each parameter being calculated from said active component using a semi-empiric formula applicable to integral bioimpedance measurements, the computer being further coupled to a display for displaying said average value.

16. The system according to claim 15, comprising a plurality of electrodes for multi-channel bioimpedance measurement, said electrodes including four basic electrodes applied to distal parts of arms and legs, respectively, of the individual;

a pair of auxiliary electrodes for measuring a skin resistance of the individual and being applied to two of arms and legs of the individual and positioned more distal than corresponding basic electrodes;

four additional electrodes located one on each of a hip and a shoulder of the individual; and automatic multiplexing means for performing said multi-channel bioimpedance measurements.

* * * * *